United States Patent
Toda et al.

(10) Patent No.: US 10,610,762 B2
(45) Date of Patent: Apr. 7, 2020

(54) EXERCISE INFORMATION MEASUREMENT APPARATUS, EXERCISE ASSISTANCE METHOD, AND EXERCISE ASSISTANCE PROGRAM

(71) Applicant: OMRON HEALTHCARE CO., LTD., Muko-shi, Kyoto (JP)

(72) Inventors: Shinichi Toda, Kyoto (JP); Takehiro Hamaguchi, Kyoto (JP); Naoki Takeishi, Kyoto (JP); Mitsuru Samejima, Kyoto (JP); Nobuki Yakura, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 259 days.

(21) Appl. No.: 15/793,183

(22) Filed: Oct. 25, 2017

(65) Prior Publication Data
US 2018/0065025 A1 Mar. 8, 2018

Related U.S. Application Data

(63) Continuation of application No. PCT/JP2016/061938, filed on Apr. 13, 2016.

(30) Foreign Application Priority Data

Apr. 27, 2015 (JP) .................................. 2015-090524

(51) Int. Cl.
*G16H 20/30* (2018.01)
*A63B 71/06* (2006.01)
(Continued)

(52) U.S. Cl.
CPC ...... *A63B 71/0622* (2013.01); *A63B 24/0062* (2013.01); *A63B 24/0084* (2013.01);
(Continued)

(58) Field of Classification Search
CPC ............ A63B 71/0622; A63B 24/0062; A63B 24/0084; A63B 24/0087; A63B 24/0075;
(Continued)

(56) References Cited

FOREIGN PATENT DOCUMENTS

| JP | H08-052244 | 2/1996 |
| JP | 2002-346013 A | 12/2002 |

(Continued)

OTHER PUBLICATIONS

Bai et al., Using a Three-Axis Accelerometer and GPS Module in a Smart Phone to Measure Walking Steps and Distance, 2014 IEEE 27th Canadian Conference on Electrical and Computer Engineering (CCECE), 6 pp. (Year: 2014).*

(Continued)

*Primary Examiner* — Toan M Le
(74) *Attorney, Agent, or Firm* — Oliff PLC

(57) ABSTRACT

An exercise information measurement apparatus including: an exercise information generation unit that generates exercise information based on an output of a bodily motion detection unit that detects a bodily motion; a storage unit that stores exercise model data in which an increment of the exercise information is associated with each time segment obtained by dividing a pre-set time period (24 hours); an integration value calculation unit that calculates an integration value of the increment of the exercise information corresponding to a period of time from a particular time to a current time in the exercise model data; and a display control unit that causes a display unit to display the exercise information generated by the exercise information generation unit during the period of time from the particular time to the current time and the integration value.

7 Claims, 6 Drawing Sheets

(51) Int. Cl.
*G06K 9/00* (2006.01)
*A63B 24/00* (2006.01)

(52) U.S. Cl.
CPC ......... *G06K 9/00342* (2013.01); *G16H 20/30* (2018.01); *A63B 24/0006* (2013.01); *A63B 24/0075* (2013.01); *A63B 24/0087* (2013.01); *A63B 71/0669* (2013.01); *A63B 71/0686* (2013.01)

(58) Field of Classification Search
CPC . A63B 24/0006; G06K 9/00342; G16H 20/30
See application file for complete search history.

(56) References Cited

FOREIGN PATENT DOCUMENTS

| | | |
|---|---|---|
| JP | 2008-524589 A | 7/2008 |
| JP | 2011-210119 A | 10/2011 |
| JP | 2015-058218 A | 3/2015 |

OTHER PUBLICATIONS

Jun. 14, 2016 International Search Report issued in Patent Aplication No. PCT/JP2016/061938.

* cited by examiner

FIG. 3

| MONDAY | 0-5 MIN | 5-10 MIN | 10-15 MIN | 15-20 MIN | 20-25 MIN | 25-30 MIN | 30-35 MIN | 35-40 MIN | 40-45 MIN | 45-50 MIN | 50-55 MIN | 55-60 MIN |
|---|---|---|---|---|---|---|---|---|---|---|---|---|
| 0:00-1:00 | 0 | 0 | 0 | 0 | 0 | 0 | 0 | 0 | 0 | 0 | 0 | 0 |
| 1:00-2:00 | 0 | 0 | 0 | 0 | 0 | 0 | 0 | 0 | 0 | 0 | 0 | 0 |
| 2:00-3:00 | 0 | 0 | 0 | 0 | 0 | 0 | 0 | 0 | 0 | 0 | 0 | 0 |
| 3:00-4:00 | 0 | 0 | 0 | 0 | 0 | 0 | 0 | 0 | 0 | 0 | 0 | 0 |
| 4:00-5:00 | 0 | 0 | 0 | 0 | 0 | 0 | 0 | 0 | 0 | 0 | 0 | 0 |
| 5:00-6:00 | 0 | 0 | 0 | 0 | 0 | 0 | 0 | 0 | 0 | 0 | 0 | 0 |
| 6:00-7:00 | 20 | 20 | 20 | 20 | 20 | 20 | 10 | 10 | 10 | 20 | 20 | 20 |
| 7:00-8:00 | 5 | 5 | 5 | 5 | 5 | 5 | 100 | 100 | 100 | 100 | 100 | 100 |
| 8:00-9:00 | 30 | 30 | 30 | 30 | 30 | 5 | 5 | 5 | 5 | 5 | 5 | 5 |
| 9:00-10:00 | 7 | 7 | 7 | 7 | 7 | 7 | 7 | 7 | 7 | 7 | 7 | 4 |
| 10:00-11:00 | 0 | 0 | 0 | 0 | 0 | 0 | 0 | 0 | 0 | 0 | 0 | 7 |
| 11:00-12:00 | 3 | 3 | 3 | 3 | 3 | 3 | 3 | 3 | 3 | 3 | 3 | 0 |
| 12:00-13:00 | 30 | 30 | 30 | 30 | 30 | 30 | 30 | 30 | 30 | 30 | 30 | 3 |
| 13:00-14:00 | 30 | 30 | 30 | 30 | 30 | 30 | 30 | 30 | 30 | 30 | 30 | 30 |
| 14:00-15:00 | 5 | 5 | 5 | 5 | 5 | 100 | 100 | 100 | 100 | 100 | 100 | 30 |
| 15:00-16:00 | 30 | 30 | 30 | 30 | 30 | 0 | 0 | 0 | 0 | 0 | 0 | 5 |
| 16:00-17:00 | 5 | 5 | 5 | 5 | 5 | 5 | 5 | 5 | 5 | 5 | 5 | 100 |
| 17:00-18:00 | 30 | 30 | 30 | 30 | 30 | 30 | 30 | 30 | 30 | 30 | 30 | 0 |
| 18:00-19:00 | 5 | 5 | 5 | 5 | 5 | 0 | 0 | 0 | 0 | 0 | 0 | 5 |
| 19:00-20:00 | 30 | 30 | 30 | 30 | 30 | 0 | 0 | 0 | 30 | 30 | 30 | 0 |
| 20:00-21:00 | 30 | 30 | 0 | 0 | 0 | 0 | 0 | 0 | 0 | 0 | 0 | 0 |
| 21:00-22:00 | 0 | 0 | 0 | 0 | 0 | 0 | 0 | 0 | 0 | 0 | 0 | 0 |
| 2:00-23:00 | 0 | 0 | 0 | 0 | 0 | 0 | 0 | 0 | 0 | 0 | 0 | 0 |
| 23:00-24:00 | 0 | 0 | 0 | 0 | 0 | 0 | 0 | 0 | 0 | 0 | 0 | 0 |

5a

EXERCISE INFORMATION MEASUREMENT APPARATUS, EXERCISE ASSISTANCE METHOD, AND EXERCISE ASSISTANCE PROGRAM

TECHNICAL FIELD

The present invention relates to an exercise information measurement apparatus, an exercise assistance method, and an exercise assistance program.

BACKGROUND ART

In recent years, exercise information measurement apparatuses that can measure exercise information such as step count, walking distance, and expended calories by using a motion detection sensor that detects bodily motion, such as an acceleration sensor or an angular velocity sensor, have been actively developed.

An exercise information measurement apparatus is known with which the user can perform exercise while competing with pre-stored exercise model data.

For example, Patent Document 1 discloses a system in which a plurality of exercise models are generated from exercise data obtained through measurement while the user, other users, celebrities and the like are actually exercising, and stored, and a virtual runner is displayed based on the exercise model selected from among the plurality of stored exercise models such that the user can perform exercise together with the virtual runner.

Patent Document 2 discloses an activity amount meter in which, when a marathon mode is set, the positions of the user and a virtual runner are displayed on a virtual marathon course, and the positions change in real time according to the time that has elapsed after setting the marathon mode and the amount of exercise performed by the user.

CITATION LIST

Patent Literature

Patent Document 1: JP 2011-210119A
Patent Document 2: JP2002-346013A

SUMMARY OF INVENTION

Technical Problem

In the system disclosed in Patent Document 1, a user's moving distance is calculated from the point in time when the user starts exercise, the position of the user is displayed in a virtual space according to the user's moving distance, and the position of the virtual runner is displayed based on exercise model data in which the time elapsed from the start of exercise and the moving distance are associated with each other.

Likewise, in the activity amount meter disclosed in Patent Document 2, from the point in time at which the marathon mode was started, the position of the user in the virtual course changes according to the amount of exercise performed by the user, and the position of the virtual runner changes based on data in which the time that has elapsed from the start of the marathon mode and the moving distance are associated with each other.

According to Patent Documents 1 and 2, the moving distance of the virtual runner changes according to the time that has elapsed from the start of the exercise mode. Accordingly, the virtual runner moves in the same pattern regardless of the start time of the exercise mode.

For example, in the case where the exercise mode is started late at night, the user's moving distance does not increase while the user is asleep, but the virtual runner keeps moving, as a result of which, it is not possible to compete under the same conditions. Patent Documents 1 and 2 are made on the assumption that the user who has decided to perform exercise starts the exercise mode and competes with the virtual runner, and thus no consideration is given to a situation in which the user competes with the virtual runner while performing daily activities.

The present invention has been made in view of the circumstances described above, and it is an object of the present invention to provide an exercise information measurement apparatus, an exercise assistance method, and an exercise assistance program that enable a user to battle against an exercise model while performing daily activities and increase the user's motivation to exercise.

Solution to the Problem

An exercise information measurement apparatus according to the present invention includes: an exercise information generation unit that generates exercise information based on an output of a bodily movement detection unit that detects a bodily motion; a storage unit that stores exercise model data in which an increment of the exercise information is associated with each of time segments obtained by dividing a pre-set time period; an integration value calculation unit that calculates an integration value of the increment corresponding to a period of time from a particular time to a current time in the exercise model data; and a display control unit that causes a display unit to display an image for comparison between the exercise information generated by the exercise information generation unit during the period of time from the particular time to the current time and the integration value calculated by the integration value calculation unit.

An exercise assistance method according to the present invention includes: an exercise information generation step of generating exercise information based on an output of a bodily motion detection unit that detects bodily motion; an integration value calculation step of acquiring exercise model data from a storage unit storing the exercise model data in which an increment of the exercise information is associated with each time segment obtained by dividing a pre-set time period, and calculating an integration value of the increment corresponding to a period of time from a particular time to a current time in the acquired exercise model data; and a display control step of causing a display unit to display an image for comparison between the exercise information generated in the exercise information generation step during the period of time from the particular time to the current time and the integration value calculated in the integration value calculation step.

An exercise assistance program according to the present invention is a program for causing a computer to execute the steps of the above-described exercise assistance method.

Advantageous Effects of the Invention

According to the present invention, it is possible to provide an exercise information measurement apparatus, an exercise assistance method, and an exercise assistance program that enable a user to battle against an exercise model while performing daily activities and increase the user's motivation to exercise.

BRIEF DESCRIPTION OF DRAWINGS

FIG. 3 is a diagram showing an example of exercise model data stored in the storage unit 5 included in the exercise information measurement apparatus 10 shown in FIG. 1.

DESCRIPTION OF EMBODIMENTS

Hereinafter, embodiments of the present invention will be described with reference to the drawings.

Figure 1:
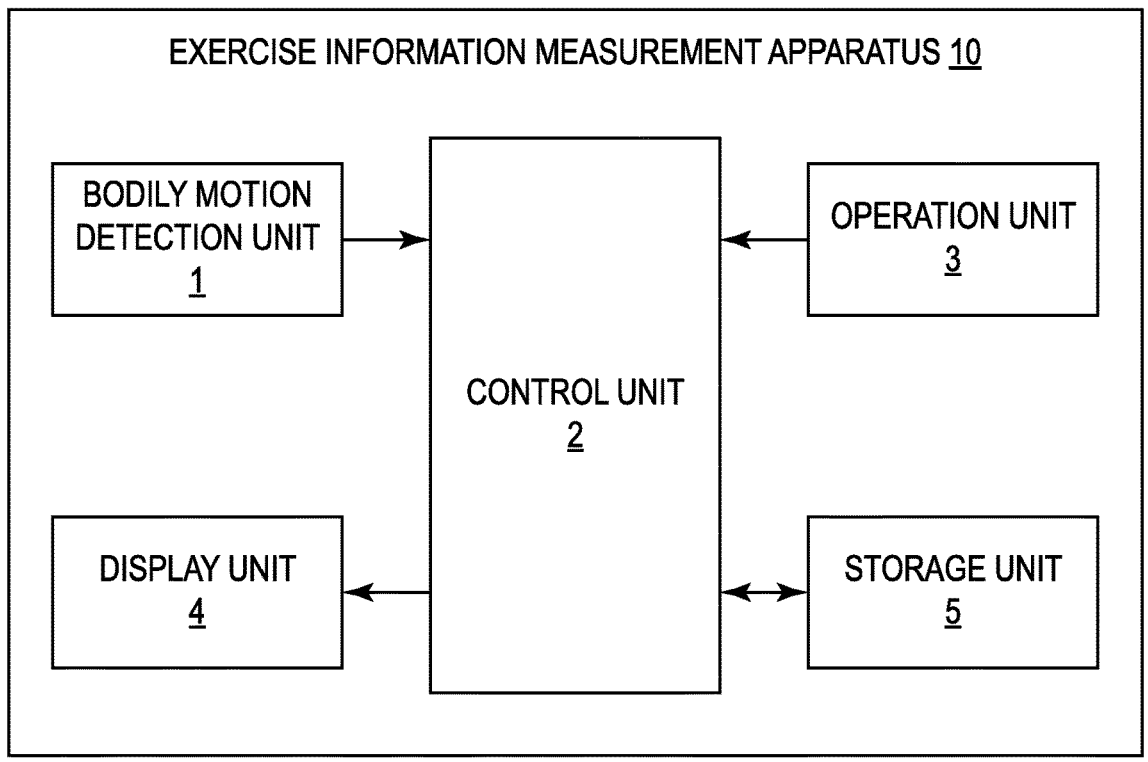
FIG. 1 is a block diagram showing a configuration example of an exercise information measurement apparatus 10, which is provided to illustrate an embodiment of the present invention.

FIG. 1 is a block diagram showing a configuration of an exercise information measurement apparatus 10, which is provided to illustrate an embodiment of the present invention. The exercise information measurement apparatus 10 is used attached to the body of the user (including a state of being inserted in a pocket of an article of clothing or in a bag of the user). Specific examples include a pedometer, an activity amount meter, and a sports watch.

The exercise information measurement apparatus 10 includes a bodily motion detection unit 1, a control unit 2 that performs overall control, an operation unit 3, a display unit 4 for displaying various types of information, and a storage unit 5 that includes a storage medium such as a flash memory or a ROM (Read Only Memory) and a driver that controls reading and writing with respect to the storage medium.

The bodily motion detection unit 1 detects bodily motion information (acceleration, angular velocity, and the like) according to the motion of the user wearing the exercise information measurement apparatus 10 (including a state in which the exercise information measurement apparatus 10 is inserted in a pocket of an article of clothing).

The bodily movement detection unit 1 includes various sensors such as an acceleration sensor and an angular velocity sensor, and a signal processing unit that processes signals output from the various sensors. It is sufficient that the bodily motion detection unit 1 includes at least one motion sensor and a signal processing unit that processes signals from the motion sensor.

The control unit 2 is composed mainly of a processor that executes a program stored in the ROM included in the storage unit 5.

The operation unit 3 is a device for inputting various instructions to the control unit 2, and is composed of a button, a touch panel provided on the display unit 4, and the like.

The storage unit 5 stores the bodily motion information (acceleration information and angular velocity information) detected by the bodily motion detection unit 1 and stores information needed for operations performed by the exercise information measurement apparatus 10.

Figure 2:
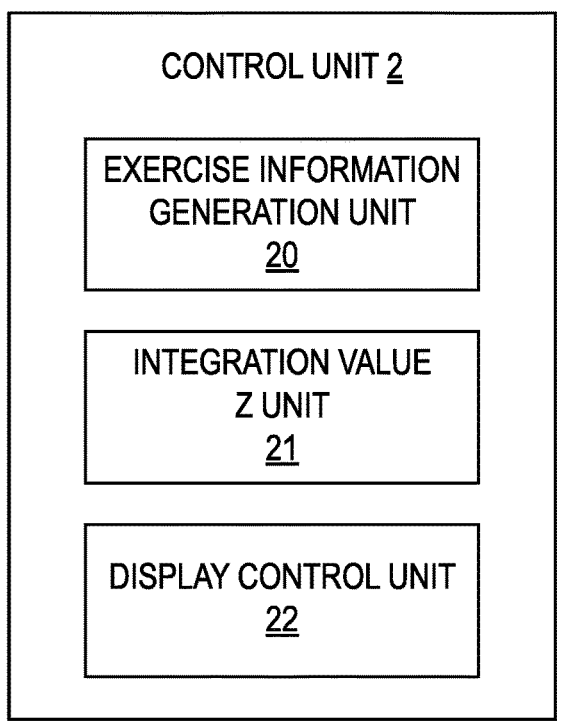
FIG. 2 is a diagram showing functional blocks that are implemented by a control unit 2 as a result of a processor executing a program stored in a storage unit 5 included in the exercise information measurement apparatus 10 shown in FIG. 1.

FIG. 2 is a diagram showing functional blocks implemented by the control unit 2 as a result of the processor executing an exercise assistance program stored in the storage unit 5 in the exercise information measurement apparatus 10 shown in FIG. 1.

As shown in FIG. 2, the control unit 2 includes an exercise information generation unit 20, an integration value calculation unit 21, and a display control unit 22.

The exercise information generation unit 20 generates exercise information (information indicating how much exercise was performed) regarding the user of the exercise information measurement apparatus 10 based on the bodily motion information detected by the bodily motion detection unit 1.

To be specific, the exercise information generation unit 20 calculates, based on the bodily motion information, the step count, moving distance, or expended calories of the user for a predetermined length of time as exercise information.

The exercise information measurement apparatus 10 has a battle mode in which a battle against a virtual opponent (hereinafter referred to as "agent") is performed. The storage unit 5 stores, as data for use in the battle mode, exercise model data in which an increment of exercise information (in the following description, step count is used as an example) is associated with a time segment obtained by dividing a pre-set time period on a calendar.

The exercise model data is data in which the agent's activities are defined, and the exercise information measurement apparatus 10 is configured such that, when the battle mode is started and an instruction to start a battle is issued, the agent starts a virtual activity in accordance with the exercise model data, and the user can compete for step count for a fixed length of time from the start of the battle against the step count of the agent counted from when the agent started the activity.

In the present embodiment, the pre-set time period on the calendar can be set to, for example, 1 day (24 hours), 1 week (7 days), 1 month (30 days), 1 year (365 days), or the like, but is not limited thereto. The pre-set time period is preferably set to 1 day or more, considering the purpose of the battle mode is to have fun battling against the agent while performing daily activities. Also, the time segment can be set to, for example, 1 minute, 5 minutes, 10 minutes, or the like, but is not limited thereto.

As described above, the exercise model data stored in the storage unit 5 is data in which times of 1 day, 1 week, 1 month, 1 year, or the like that are periods on a calendar and the increment in step count are associated with each other.

FIG. 3 is a diagram showing an example of exercise model data 5a stored in the storage unit 5.

In the exercise model data 5a shown in FIG. 3, Monday (1 day) on the calendar is divided every 5 minutes, and the increment in step count is associated with each 5 minute time segment, and stored.

In the exercise model data 5a, the "n:00-m:00" column (n=0 to 23, and m=1 to 24) indicates 1 hour (a period between n:00:01 and m:00:00) from n o'clock to m o'clock on Monday.

In the exercise model data 5a, the time segment indicated by "α-β min" (α=0, 5, 10, 15, 20, 25, 30, 35, 40, 45, 50, and 55; and β=5, 10, 15, 20, 25, 30, 35, 40, 45, 50, 55, and 60) indicates a period from α min or more and less than β minutes (a period from α min 1 sec to β min 0 sec).

For example, during a period between 0:00:01 and 7:30:00 on Monday, the increment in step count every 5 minutes is set to 0 because a setting has been made such that the exercise model is in sleep. After 7:30:01 on Monday, the increment in step count every 5 minutes is set to a value greater than 0 because a setting has been made such that the exercise model starts an activity.

The exercise model data 5a is data in which the activity of the agent is defined such that, for example, the step count is incremented by 10 when 5 minutes from 7:30:01 to 7:35:00 has elapsed, and the step count is further incremented by 10 when 5 minutes from 7:35:01 to 7:40:00 has elapsed.

The exercise model data 5a is one week's worth of data, and thus although not shown in the diagram, data on Tuesday, Wednesday, Thursday, Friday, Saturday, and Sunday are also stored in the storage unit 5. Note, however, that the value of the increment in step count in each time segment is different depending on the day of the week.

In the storage unit 5, a plurality of exercise model data sets each including one week's worth of data are stored, and the user can select a particular exercise model data set from among the plurality of exercise model data sets. The plurality of exercise model data sets have different patterns in the increment in step count corresponding to each time segment.

For example, in the case of exercise model data set for a salaried worker who has Saturdays and Sundays off, the exercise model data is set such that, on Saturday and Sunday, the sleeping time (the period during which the step count increment is set to 0) is longer and the step count as a whole is higher than those of the weekdays.

Likewise, in the case of exercise model data set for a salaried worker who has Sundays off, the exercise model data is set such that, on Sunday, the sleeping time is longer and the step count as a whole is higher than those of the weekdays and Saturday.

In response to the user starting the battle mode, the integration value calculation unit 21 acquires, from the storage unit 5, exercise model data designated by the user. The integration value calculation unit 21 calculates an integration value of the increments in step count (cumulative step count) corresponding to a period of time from a particular time to the current time in the acquired exercise model data.

As used herein, the term "particular time" refers to a battle start time at which the user performs an operation to provide an instruction to start a battle against the agent in a state in which the exercise information measurement apparatus 10 has been set to the battle mode, and is a timing that can be determined by the user.

For example, a case will be considered where the battle start time is 8:33:00 on Monday. Referring to the exercise model data 5a, 20 is stored as the increment in the step count of the agent in a time segment between 8:30:01 and 8:35:00 that includes the battle start time.

The integration value calculation unit 21 calculates, from a step count of 20 that corresponds to the time segment between 8:30:01 and 8:35:00, the increment in the step count of the agent per unit time (for example, 1 minute) during this time segment (=20 (steps)/5 (minutes)=4 (steps)). Also, the integration value calculation unit 21 sets the step count of the agent at the battle start time to 0.

At 8:34:00, which is one minute after the battle start time, the integration value calculation unit 21 adds the increments in step count of every minute (=4) to the step count at 8:33:00 (=0) so as to obtain a step count of 4.

After another minute, at 8:35:00, the integration value calculation unit 21 adds the increments in the step count of every minute (=4) to the step count at 8:34:00 so as to obtain a step count of 8.

Subsequently, at 8:36:00, the integration value calculation unit 21 calculates, from a step count of 100 that corresponds to a time segment between 8:35:01 and 8:40:00, the increments in step count of the agent every one minute (=100 (steps)/5 (minutes)=20 (steps)). Then, the integration value calculation unit 21 adds the resulting increments in step count of every minute (=20) to the step count at 8:35:00 (=8) so as to obtain a step count of 28.

In this way, each time a certain amount of time has elapsed from the battle start time, the step count of the agent is increased by the integration value calculation unit 21 in accordance with the exercise model data.

The display control unit 22 causes the display unit 4 to display both the step count of the user from the battle start time, which was generated by the exercise information generation unit 20, and the step count of the agent from battle start time, which was calculated by the integration value calculation unit 21.

In order to improve the battle accuracy, in the integration value calculation unit 21, the unit time may be set to the update interval for updating the display screen of the display unit 4 (for example, 0.25 seconds).

Figure 4:
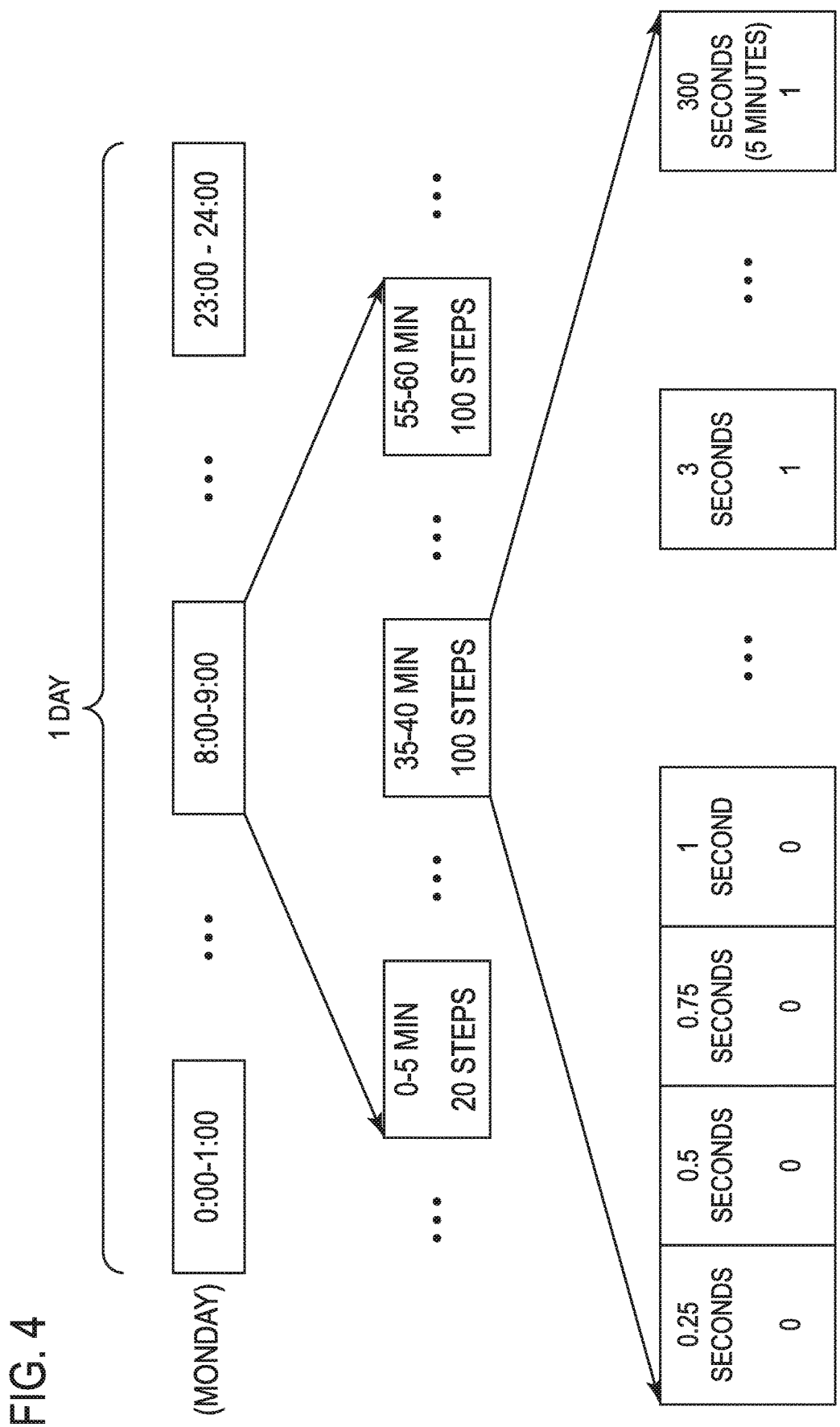
FIG. 4 is a diagram illustrating integration value calculation processing with a display update timing of every 0.25 seconds performed by an integration value calculation unit 21 shown in FIG. 2.

In this case, for example, as shown in FIG. 4, the integration value calculation unit 21 may be configured to, in the time segment between 8:35:01 and 8:40:00, update the step count of the agent every 0.25 seconds by obtaining the step count increment every 0.25 seconds through calculation (=100 (steps)/(300 (seconds)/0.25 (seconds)) ≈0.083 (steps)). With this configuration, the step count of the agent can be updated at a timing at which the display of the step count of the user is updated, and it is therefore possible to give the user a feeling as if he/she is realistically competing against the agent.

A description will be given of operations performed by the exercise information measurement apparatus 10 configured as described above.

Figure 5:
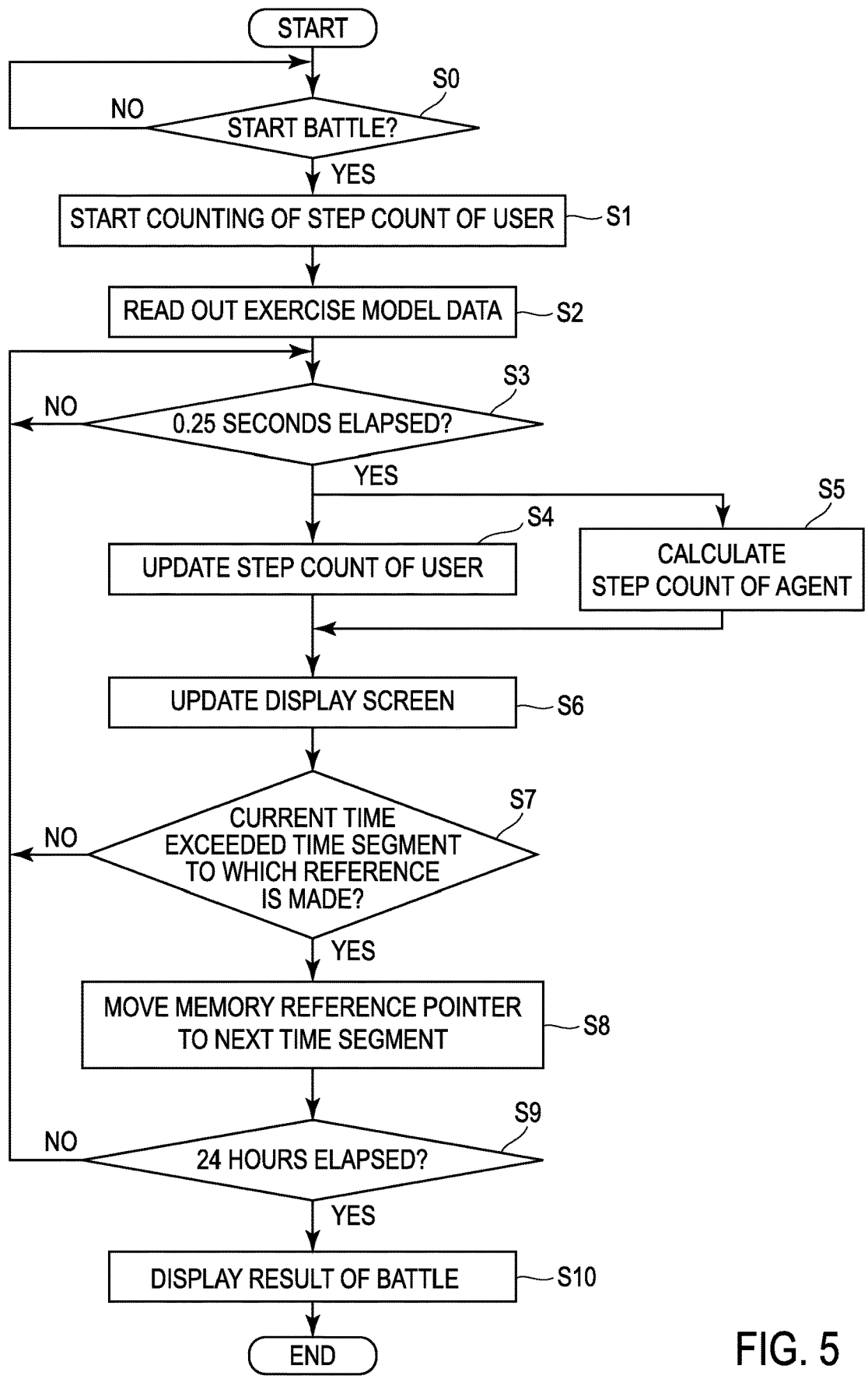
FIG. 5 is a flowchart illustrating operations performed by the exercise information measurement apparatus 10.

FIG. 5 is a flowchart illustrating operations performed by the exercise information measurement apparatus 10. FIG. 5 shows an operation example in which the unit time is set to 0.25 seconds.

First, the user wears the exercise information measurement apparatus 10 and sets the battle mode. In the battle mode, the user can select the duration of a battle against the agent from either 1 day (24 hours) or 1 week (7 days). In FIG. 5, operations performed when the battle duration is set to 1 day will be described. Also, in the battle mode, the user can designate one from among a plurality of exercise model data sets by operating the operation unit 3.

The control unit 2 of the exercise information measurement apparatus 10 determines whether or not an instruction to start a battle against an agent that virtually performs an activity in accordance with the exercise model data designated by the user has been made through operation of the operation unit 3, and waits for an instruction to start a battle to be received (step S0).

If an affirmative determination (YES) is made in step S0, the control unit 2 causes the exercise information generation unit 20 to start counting the step count of the user wearing the exercise information measurement apparatus 10 (step S1). It is assumed here that the time at which the instruction to start a battle is issued (battle start time) is, for example, 8:33 on Monday.

The control unit 2 reads out exercise model data designated by the user (here, the exercise model data including the exercise model data 5*a* shown in FIG. 3) (step S2), and sets a memory reference pointer in the read-out exercise model data to the time segment between 8:30:01 and 8:35:00 on Monday that includes the battle start time.

The memory reference pointer is a pointer for designating from which time segment data of the exercise model data should be read. The control unit 2 moves the memory reference pointer from a particular time segment to the next time segment along with the elapse of time.

Subsequently, the control unit 2 determines whether or not 0.25 seconds, which is the display update interval of the display unit 4, has elapsed, and waits for 0.25 seconds to elapse (step S3).

If an affirmative determination (YES) is made in step S3, the exercise information generation unit 20 generates the step count of the user at this time (the step count of the user wearing the exercise information measurement apparatus 10 during a period of time from the battle start time to this time) (step S4).

In parallel to step S4, the integration value calculation unit 21 calculates the increment in step count, every 0.25 seconds from the increment in step count corresponding to the time segment designated by the memory reference pointer. Then, the integration value calculation unit 21 adds the calculated increment in step count to the step count of the agent so as to calculate the latest step count of the agent (step S5).

For example, the step count per 0.25 seconds during the time segment between 8:30:01 and 8:35:00 is as follows: 20 (steps)/{300 (seconds)/0.25 (seconds)}≈0.016 (steps).

Accordingly, the integration value calculation unit 21 adds 0.016 to the step count each time 0.25 seconds has elapsed from the battle start time. The step count of the agent at the battle start time is set to an initial value of 0.

After processing of steps S4 and S5 has been performed, the display control unit 22 of the exercise information measurement apparatus 10 causes the display unit 4 to display both the step count of the user generated in step S4 and the step count of the agent generated in step S5 (step S6).

Figure 6:
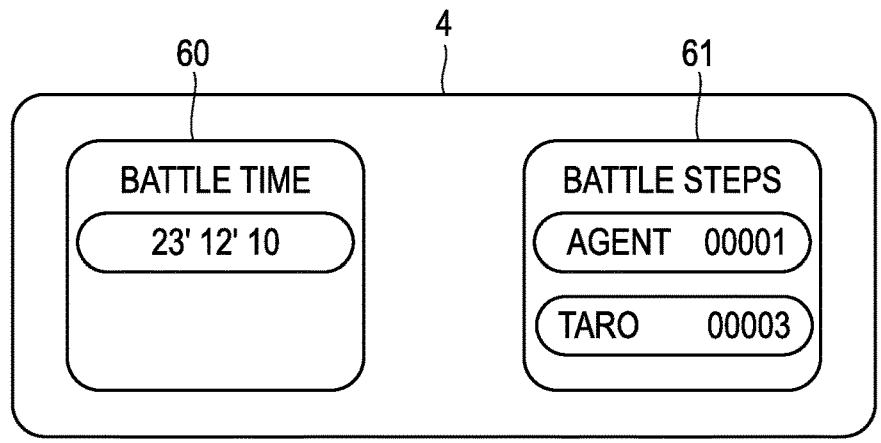
FIG. 6 is a diagram showing an example of a screen displayed on a display unit 4 included in the exercise information measurement apparatus 10.

FIG. 6 is a diagram showing an example of a screen displayed on the display unit 4 of the exercise information measurement apparatus 10.

As shown in FIG. 6, on the display unit 4, a display screen 60 for displaying the remaining time of the battle and a display screen 61 for displaying the step count of the user and the step count of the agent are displayed.

In the display screen 60, "23'12'10 (23 hours, 12 minutes, and 10 seconds)" is displayed as the remaining time of the battle. In the display screen 61, "00001" is displayed as the step count of the agent, and "00003" is displayed as the step count of the user (user name: TARO).

The user wearing the exercise information measurement apparatus 10 can easily compare his/her step count with the step count of the agent that is the opponent and easily recognize the remaining time of the battle by looking at the screen shown in FIG. 6.

Next, the control unit 2 of the exercise information measurement apparatus 10 determines whether or not the current time has exceeded the time segment to which reference is made with the memory reference pointer (step S7). If it is determined that the current time has not exceeded the time segment to which reference is made (NO in step S7), the processing returns to step S3, and the above-described processing is repeatedly executed.

If an affirmative determination (YES) is made in step S7, the control unit 2 of the exercise information measurement apparatus 10 moves the memory reference pointer to the next time segment so as to make reference to the next time segment (step S8).

For example, if the current time exceeds 8:35:00, the memory reference pointer is moved to a time segment between 8:35:01 and 8:40:00, and reference is made to the step count increment in the time segment.

If the current time exceeds 24:00:00, the control unit 2 moves the memory reference pointer to the first time segment of Tuesday.

The control unit 2 of the exercise information measurement apparatus 10 determines whether or not 24 hours has elapsed from the battle start time (step S9). If it is determined that 24 hours has not yet elapsed (NO in step S9), the processing returns to step S3, and the above-described processing is repeatedly executed.

If an affirmative determination (YES) is made in step 9, the display control unit 22 causes the display unit 4 to display the result of the battle (step S10).

Figure 7A:
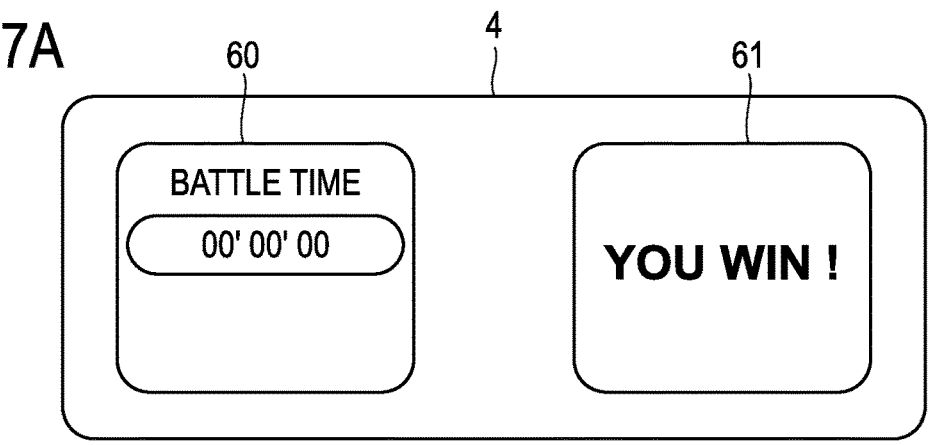
FIGS. 7(A) and 7(B) are diagrams showing examples of screens displayed on the display unit 4 included in the exercise information measurement apparatus 10.
Figure 7B:
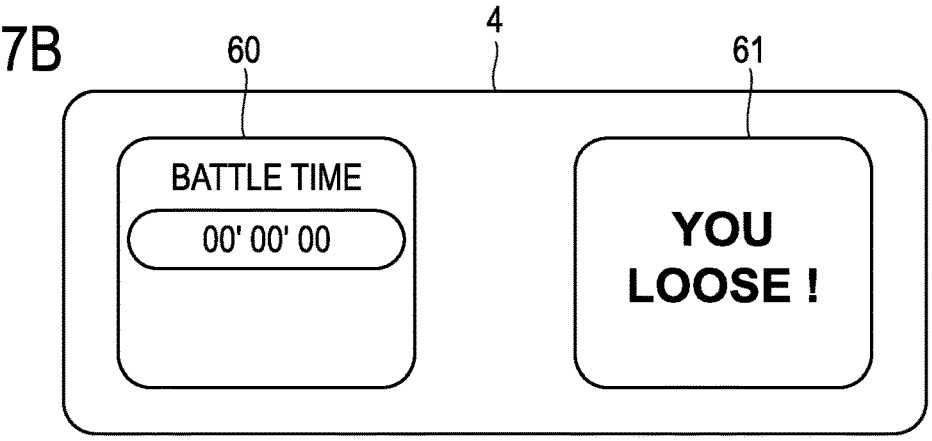

FIGS. 7(A) and 7(B) are diagrams showing examples of screens displayed on the display unit 4 of the exercise information measurement apparatus 10.

As shown in FIGS. 7(A) and 7(B), on the display unit 4, a display screen 60 for displaying the remaining time of the battle and a display screen 61 for displaying the result of the battle are displayed.

In the display screen 60, "00'00'00 (0 hours, 0 minutes, and 0 seconds)" is displayed as the remaining time of the battle. In the display screen 61, a message "YOU WIN!" or "YOU LOSE!" is displayed as the result of the battle indicating whether the user won or lost.

As described above, with the exercise information measurement apparatus 10, in the battle mode, the step count of the agent is updated each time a certain amount of time elapses in accordance with the increment in step count corresponding to each time segment during a period of time from a particular time (battle start time) in the exercise model data stored in the storage unit 5 until when the duration designated by the user (24 hours in the example shown in FIG. 5) has elapsed.

Then, each time 0.25 seconds has elapsed from the battle start time, both the step count of the agent and the step count of the user at that point in time are displayed on the display unit 4. The user can perform daily activities while comparing his/her step count with the step count of the agent. Accordingly, the user can actively perform exercise while trying to surpass the step count of the agent. It is therefore possible to improve the user's motivation to exercise.

Also, in the exercise information measurement apparatus 10, even if the battle duration is the same (for example, 1 day), depending on the battle start time, the step count of the agent is not necessarily changed in the same manner.

For example, if the battle start time is 23:00:00, in the example shown in FIG. 3, the increment in step count of the agent corresponding to the time segment is set to 0 for a while after the battle start time. Accordingly, the step count of the agent remains 0 for, for example, 6 hours after the battle start time.

In contrast, if the battle start time is 8:00:00, in the example shown in FIG. 3, the step count of the agent gradually keeps increasing for, for example, 6 hours after the battle start time.

According to the techniques disclosed in Patent Documents 1 and 2, the moving distance of the virtual opponent changes in the same manner according to the time that has elapsed from the start of a battle irrespective of whether the battle starts midnight or during the day.

With the exercise information measurement apparatus 10, the step count of the agent is changed according to one's lifestyle pattern in the real world. Accordingly, the user can realistically enjoy the battle against the agent while performing daily activities, for a long period of time such as 1 day or 1 week.

The exercise information measurement apparatus 10 may be configured such that additional exercise model data is downloaded from a predetermined website and stored. With this configuration, it is possible to make the battle mode less boring.

In the example shown in FIG. 6, the display control unit 22 causes the display unit 4 to display the step count of the agent and the step count of the user by using numerical values, but a gauge corresponding to the numerical values may be displayed on the display unit 4. Alternatively, the higher step count may be displayed in a highlighted manner so as to allow the user to easily recognize which of the agent and the user is in the lead.

The display screen 61 shown in FIG. 6 or the gauge described above constitute an image for comparison between the step count of the agent and the step count of the user.

In the exercise information measurement apparatus 10, it is possible to set the battle duration to 1 week. In this case, a configuration may be used in which in a state in which the memory reference pointer is set to the last time segment on Sunday in one week's worth of exercise model data, if the current time exceeds this time segment, the memory reference pointer is moved to the first time segment on Monday.

Also, in this configuration, by continuously moving the memory reference pointer in one week's worth of data, the battle can be performed for a period of time longer than 1 week (for example, 1 month, or 1 year). It is of course possible to store one month's worth of data or one year's worth of data in advance in the storage unit 5 as exercise model data.

Also, with the exercise information measurement apparatus 10, one week's worth of data is stored in the storage unit 5 as exercise model data, but one day's worth of exercise model data may be stored.

In this case, a configuration may be used in which, in a state in which the memory reference pointer is set to the last time segment in the exercise model data, if the current time exceeds this time segment, the memory reference pointer is moved back to the first time segment in the exercise model data. With this configuration, it is possible to cope with a situation in which the battle duration is set to a period of time longer than 1 day.

The operation example shown in FIG. 5 was described assuming that the user performs a battle against the agent in terms of step count as a battle category. It is also possible to use a configuration in which a settings menu may be provided so as to allow the user to select one from among exercise information such as step count, moving distance, expended calories, and the like, as a battle category so that the user can freely select the battle category.

As the exercise model data in this case, exercise model data in which the increment of moving distance or expended calories is associated with each time segment may be further stored.

It is also possible to use a configuration in which a conversion expression for converting the increment of moving distance or the increment of expended calories based on the increment in step count is stored in advance, and the increment of moving distance or the increment of expended calories is obtained through a mathematical operation based on the exercise model data including the increment in step count. With this configuration, by using only the exercise model data including the increment in the step count, it is possible to cope with a situation in which moving distance or expended calories is set as the battle category.

Figure 8:
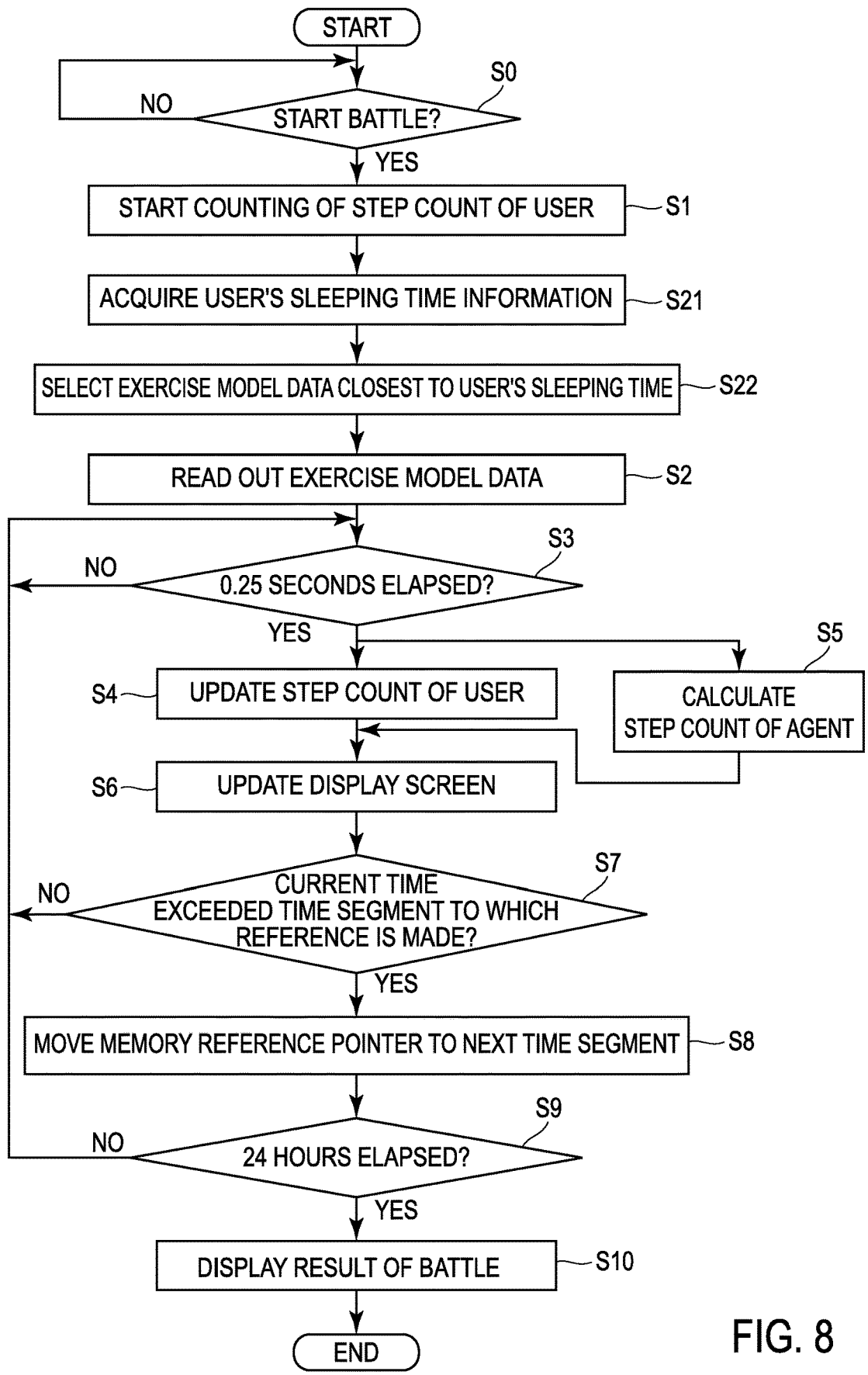
FIG. 8 is a flowchart illustrating operations performed by the exercise information measurement apparatus 10.

FIG. 8 is a flowchart illustrating a variation of the operations performed by the exercise information measurement apparatus 10 shown in FIG. 1. In FIG. 8, processing operations that are the same as those of FIG. 5 are given the same reference numerals, and a description thereof is omitted here.

To start this processing, the control unit 2 identifies the sleeping time in each of the plurality of exercise model data sets stored in the storage unit 5.

As used herein, the term "sleeping time" refers to a one-week average value of the length of a period during which a step count of 0 is set for a predetermined length of time or more in one day's worth of exercise model data (in the example shown in FIG. 3, a period between 21:50:01 and 7:30:00).

Also, even in a state in which the battle mode is not set, the exercise information generation unit 20 of the exercise information measurement apparatus 10 calculates the sleeping time of the user by using a known method based on the bodily motion information detected by the bodily motion detection unit 1, and stores one week's worth of calculated sleeping time including the latest calculated sleeping time in the storage unit 5.

In step S1, after starting counting of the step count of the user, the control unit 2 of the exercise information measurement apparatus 10 acquires information regarding one week's worth of the user's sleeping time stored in the storage unit 5 (step S21).

The control unit 2 of the exercise information measurement apparatus 10 calculates an average value of the one week's worth of the user's sleeping time, and selects exercise model data having a sleeping time closest to the average value from among the plurality of exercise model data sets stored in the storage unit 5 (step S22).

Then, the control unit 2 reads out the selected exercise model data from the storage unit 5 (step S2). The processing operations after this step are the same as those described with reference to the flowchart shown in FIG. 5, and thus a description thereof is omitted here.

As described above, according to the present variation, exercise model data (agent) in which a sleeping time closest to the user's usual sleeping time has been set is automatically selected. With this configuration, it is possible to prevent the difference in magnitude between the user and the agent from becoming excessively large.

For example, if a user who sleeps for 9 hours a day has a battle against an agent that has been set to sleep for only 5 hours a day, the activity time of the agent is relatively longer. Accordingly, the difference between the step count of the agent and the step count of the user increases as days elapse. As a result, the user will never be able to beat the agent, which lowers the user's motivation to exercise.

Likewise, if a user who sleeps for 5 hours a day has a battle against an agent that has been set to sleep for 9 hours a day, the activity time of the agent is relatively shorter. Accordingly, the step count of the user will be much higher than the step count of the agent as days elapse. As a result, the user will be able to easily beat the agent, which lowers the user's motivation to exercise.

For this reason, by using a configuration as in the variation shown in FIG. 8 in which the control unit 2 automatically selects exercise model data that is closest to the user's sleeping time, it is possible to prevent the user's motivation to exercise from decreasing.

In the present variation, an example was described in which exercise model data is automatically selected according to the user's sleeping time, but the following variation is also possible.

For example, the control unit 2 may determine, based on the bodily motion information detected by the bodily motion detection unit 1, an activity trend that shows a period in which the user is most active during one day. In the case of a user who has an activity trend of walking more at night (17 o'clock to 24 o'clock) than in the day (12 o'clock to 17 o'clock), the control unit 2 may select, from among the plurality of exercise model data sets, exercise model data with a trend in which the step count increases by a greater amount at night than in the day.

As described above, the control unit 2 determines the user's lifestyle pattern such as sleeping time or activity trend, and selects exercise model data that is closest to the lifestyle pattern determined from among a plurality of exercise model data sets. It is thereby possible to improve the user's motivation to exercise while applying an appropriate amount of pressure to the user.

A program for causing a computer to execute the steps of the flowchart shown in FIG. 5 or FIG. 8 or a program for causing a computer to function as the functional blocks shown in FIG. 2 can be provided by recording the program in a computer-readable non-transitory recording medium.

Examples of such a computer-readable recording medium include an optical medium such as a CD-ROM (Compact Disc-ROM), a magnetic recording medium such as a memory card, and the like. It is also possible to provide such a program through downloading via a network.

The embodiment disclosed herein is meant to be in all ways exemplary and not limiting. The scope of the present invention is indicated not by the above description but by the appended claims and is intended to encompass all equivalent meanings of the claims and all modifications within the scope.

For example, the length of each time segment of exercise model data may be set to the same length of 0.25 seconds described above. As shown in FIG. 3, by setting the length of each time segment to be longer than the update interval of the step count of the agent, it is possible to reduce the amount of exercise model data as well as the production cost of the apparatus.

Also, the control unit 2 may temporarily store the exercise model data read out from the storage unit 5 in an internal RAM, and calculate the step count of the agent by accessing the RAM. Accordingly, by setting the length of each time segment to be longer than the update interval of the step count of the agent, the access frequency from the processor to the RAM can be reduced, as a result of which, power consumption can be reduced.

As described above, the following items are disclosed in the present specification.

An exercise information measurement apparatus according to the disclosure includes: an exercise information generation unit that generates exercise information based on an output of a bodily motion detection unit that detects bodily motion; a storage unit that stores exercise model data in which an increment of the exercise information is associated with each time segment obtained by dividing a pre-set time period; an integration value calculation unit that calculates an integration value of the increment corresponding to a period of time from a particular time to a current time in the exercise model data; and a display control unit that causes a display unit to display an image for comparison between the exercise information generated by the exercise information generation unit during the period of time from the particular time to the current time and the integration value calculated by the integration value calculation unit.

In the exercise information measurement apparatus according to the disclosure, the display control unit causes the display unit to display, as the image, the exercise information generated by the exercise information generation unit during the period from the particular time to the current time and the integration value, and updates the exercise information and the integration value displayed on the display unit each time a first time span elapses, a length of each time segment of the exercise model data is longer than the first time span, and the integration value calculation unit calculates a unit increment every time the first time span elapses in the time segment based on the increment of the exercise information corresponding to the time segment, and calculates the integration value by integrating the unit increment calculated for the time segment including the current time each time the first time span elapses from the particular time and the current time is updated.

In the exercise information measurement apparatus according to the disclosure, the storage unit stores a plurality of the exercise model data sets having different patterns in the increment of the exercise information corresponding to each time segment, and the integration value calculation unit calculates the integration value based on exercise model data designated from among the plurality of the exercise model data sets.

In the exercise information measurement apparatus according to the disclosure, the storage unit stores a plurality of the exercise model data having different patterns in the increment of the exercise information corresponding to each time segment, and the integration value calculation unit selects one from among the plurality of the exercise model data sets according to a user's lifestyle pattern and calculates the integration value based on the selected exercise model data set.

In the exercise information measurement apparatus according to the disclosure, the pre-set time period is 1 day, 1 week, 1 month, or 1 year.

An exercise assistance method according to the disclosure includes: an exercise information generation step of generating exercise information based on an output of a bodily motion detection unit that detects a bodily motion; an integration value calculation step of acquiring exercise model data from a storage unit storing the exercise model data in which an increment of the exercise information is associated with each of time segments obtained by dividing a pre-set time period, and calculating an integration value of the increment corresponding to a period of time from a particular time to a current time in the acquired exercise model data; and a display control step of causing a display unit to display an image for comparison between the exercise information generated in the exercise information generation step during the period of time from the particular time to the current time and the integration value calculated in the integration value calculation step.

An exercise assistance program according to the disclosure is a program for causing a computer to execute the steps of the above-described exercise assistance method.

INDUSTRIAL APPLICABILITY

According to the present invention, it is possible to provide an exercise information measurement apparatus, an exercise assistance method, and an exercise assistance program that enable a user to perform a battle against an exercise model while performing daily activities and increase the user's motivation to exercise.

While the present invention has been described with reference to a specific embodiment, the present invention is not limited to the embodiment, and many modifications can be made without departing from the technical idea of the disclosed invention.

The present application claims the benefit of Japanese Patent Application 2015-090524 filed on Apr. 27, 2015, which is hereby incorporated herein in its entirety.

REFERENCE SIGNS LIST

1 Bodily motion detection unit
2 Control unit
3 Operation unit
4 Display unit
5 Storage unit
10 Exercise information measurement apparatus
20 Exercise information generation unit
21 Integration value calculation unit
22 Display control unit
5a Exercise model data
60, 61 Display screen

The invention claimed is:

1. An exercise information measurement apparatus comprising:
a memory storing virtual exercise model data in which an increment of exercise information is associated with each time segment of a plurality of time segments obtained by dividing a pre-set time period into the plurality of time segments;
a processer operatively coupled to the memory, the processor being programmed to:
generate the exercise information of a user based on an output of a bodily motion sensor that detects bodily motion of the user;
calculate a virtual integration value of the increment of exercise information corresponding to a period of time from a particular time to a current time in the virtual exercise model data; and
cause a display to display an image comparing between the exercise information of the user generated during the period of time from the particular time to the current time and the calculated virtual integration value.

2. The exercise information measurement apparatus according to claim 1, wherein:
the processor is programmed to cause the display to display, as the image, the exercise information generated during the period from the particular time to the current time and the virtual integration value, and update the exercise information and the virtual integration value displayed on the display each time a first time period elapses,
a length of each time segment of the virtual exercise model data is longer than the first time period, and
the processor is programmed to (i) calculate a unit increment every time the first time period elapses in the time segment based on the increment of the exercise information corresponding to the time segment, and (ii) calculate the virtual integration value by integrating the unit increment calculated for the time segment, including the current time, each time the first time period that elapses from the particular time and the current time is updated.

3. The exercise information measurement apparatus according to claim 1, wherein:
the memory stores a plurality of the virtual exercise model data sets having different patterns in the increment of the exercise information corresponding to each time segment, and
the processor is programmed to calculate the virtual integration value based on virtual exercise model data that is designated from among the plurality of the virtual exercise model data sets.

4. The exercise information measurement apparatus according to claim 1, wherein:
the memory stores a plurality of the virtual exercise model data sets having different patterns in the increment of the exercise information corresponding to each time segment, and
the processor is programmed to select one virtual exercise model data set from among the plurality of the virtual exercise model data sets according to a lifestyle pattern of the user and calculate the virtual integration value based on the selected virtual exercise model data.

5. The exercise information measurement apparatus according to claim 1, wherein the pre-set time period is 1 day, 1 week, 1 month, or 1 year.

6. An exercise assistance method comprising:
an exercise information generation step of generating exercise information of a user based on an output of a bodily motion sensor that detects bodily motion of the user;
an integration value calculation step of acquiring virtual exercise model data from a memory storing the virtual exercise model data in which an increment of the exercise information is associated with each time segment of a plurality of time segments that are obtained by dividing a pre-set time period into the plurality of time segments, and calculating a virtual integration value of the increment of the exercise information corresponding to a period of time from a particular time to a current time in the acquired virtual exercise model data; and
a display control step of causing a display to display an image comparing between the exercise information generated during the period of time from the particular time to the current time and the calculated virtual integration value.

7. A non-transitory computer-readable storage medium storing an exercise assistance program that, when executed, causes a computer to execute the steps of the exercise assistance method according to claim 6.

* * * * *